United States Patent
Attawia et al.

(10) Patent No.: US 11,389,148 B2
(45) Date of Patent: *Jul. 19, 2022

(54) INTERVERTEBRAL DISC PUNCTURE AND TREATMENT SYSTEM

(71) Applicant: DePuy Synthes Products, Inc., Raynham, MA (US)

(72) Inventors: Mohamed Attawia, Canton, MA (US); Cynthia Lee, Jamaica Plain, MA (US); Hassan Serhan, South Eason, MA (US); Michael O'Neil, West Barnstable, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 411 days.

This patent is subject to a terminal disclaimer.

(21) Appl. No.: 16/511,470

(22) Filed: Jul. 15, 2019

(65) Prior Publication Data

US 2019/0350574 A1 Nov. 21, 2019

Related U.S. Application Data

(63) Continuation of application No. 15/061,786, filed on Mar. 4, 2016, now Pat. No. 10,349,928, which is a continuation of application No. 11/422,222, filed on Jun. 5, 2006, now abandoned.

(51) Int. Cl.
| | | |
|---|---|---|
| A61B 17/02 | (2006.01) | |
| A61F 2/46 | (2006.01) | |
| A61B 17/34 | (2006.01) | |
| A61F 2/44 | (2006.01) | |
| A61B 17/00 | (2006.01) | |

(52) U.S. Cl.
CPC ...... *A61B 17/0218* (2013.01); *A61B 17/3415* (2013.01); *A61F 2/4611* (2013.01); *A61B 2017/00026* (2013.01); *A61B 2017/00039* (2013.01); *A61B 2017/00261* (2013.01); *A61B 2017/0262* (2013.01); *A61F 2002/444* (2013.01); *A61F 2002/4627* (2013.01)

(58) Field of Classification Search
CPC   A61B 17/0218; A61B 17/3415; A61F 2/4611
USPC ........................................................ 604/264
See application file for complete search history.

(56) References Cited

U.S. PATENT DOCUMENTS

| | | |
|---|---|---|
| 4,270,535 A | 6/1981 | Bogue et al. |
| 4,791,937 A | 12/1988 | Wang |
| 5,088,982 A | 2/1992 | Ryan |
| 5,827,305 A | 10/1998 | Gordon |
| 5,871,470 A | 2/1999 | McWha |
| 6,066,122 A | 5/2000 | Fisher |
| 6,245,044 B1 | 6/2001 | Daw et al. |
| 6,497,686 B1 | 12/2002 | Adams et al. |
| 6,613,017 B1 | 9/2003 | Mickley |
| 6,695,822 B2 | 2/2004 | Adams et al. |
| 7,799,833 B2 | 9/2010 | Boyd |
| 2002/0019626 A1* | 2/2002 | Sharkey ............ A61B 17/1671 606/41 |
| 2004/0229878 A1 | 11/2004 | DiMauro et al. |

(Continued)

*Primary Examiner* — Phillip A Gray
(74) *Attorney, Agent, or Firm* — Dunlap Codding, P.C.

(57) ABSTRACT

A pre-assembled, telescoping needle system comprising an outer needle surrounding a finer gauge needle which, after percutaneous penetration by the outer needle, extends to penetrate the intervertebral disc into which the injectable is to be delivered.

20 Claims, 11 Drawing Sheets

(56) References Cited

U.S. PATENT DOCUMENTS

2005/0182454 A1* 8/2005 Gharib .................. A61B 17/00
  607/48
2005/0234425 A1 10/2005 Miller et al.

* cited by examiner

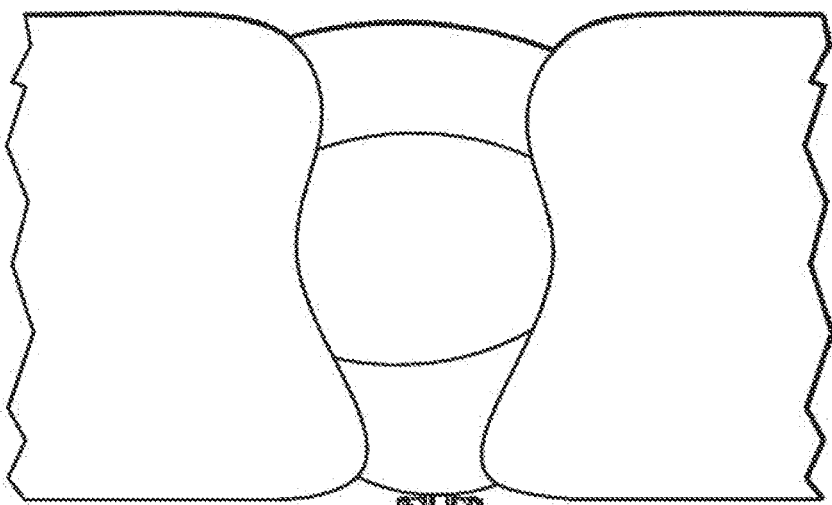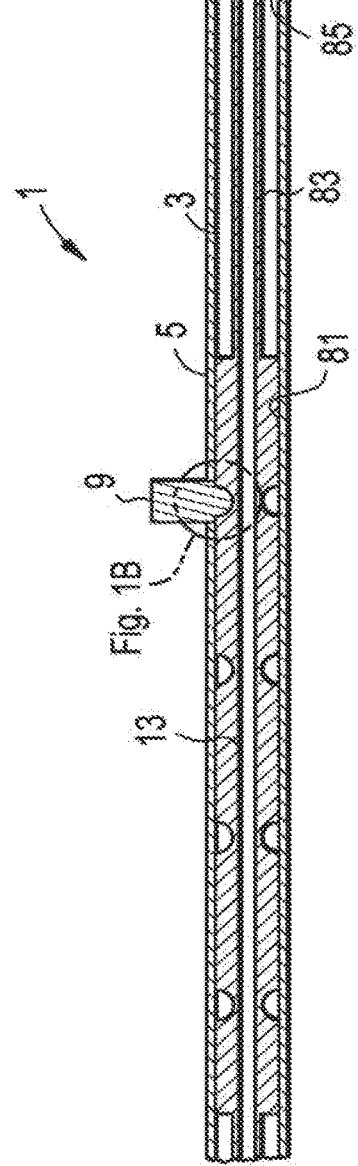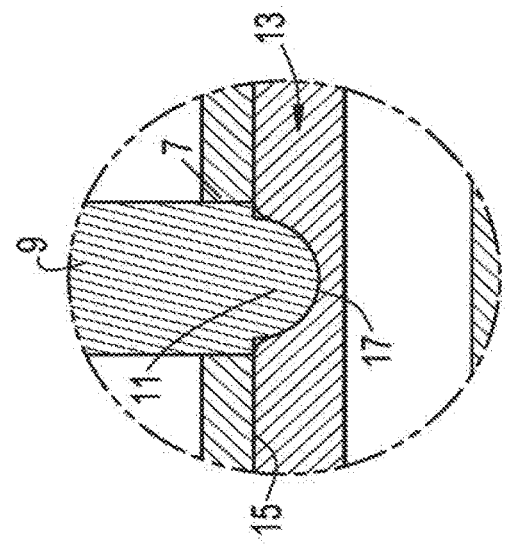

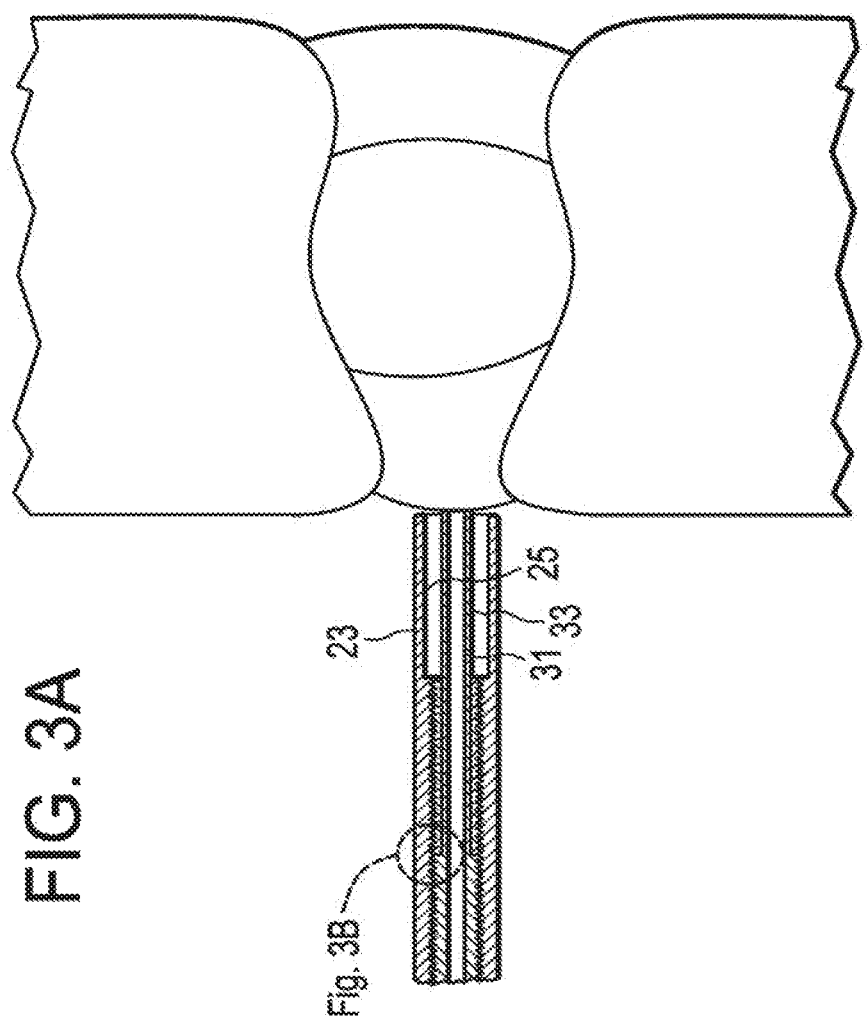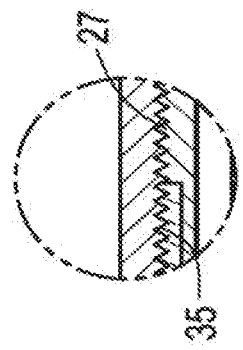

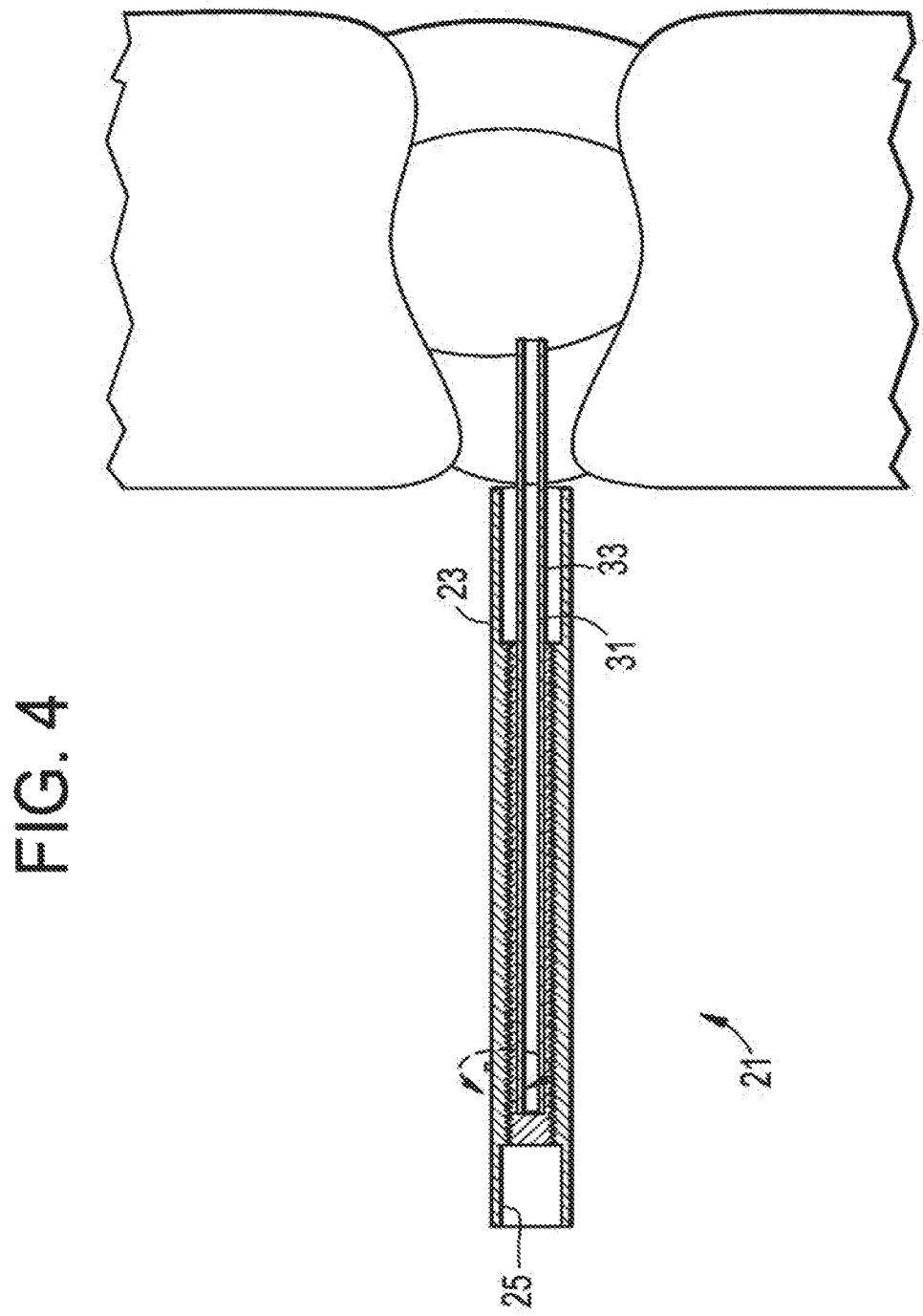

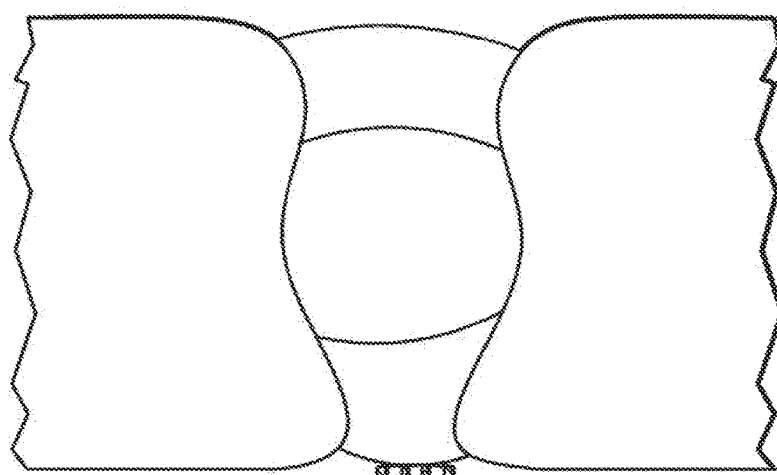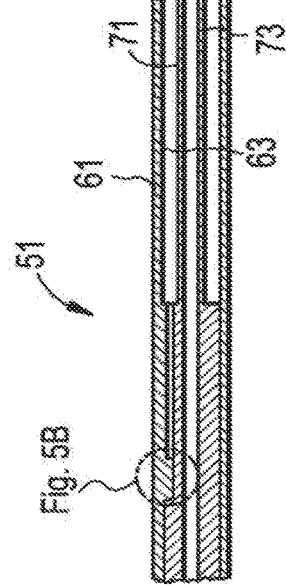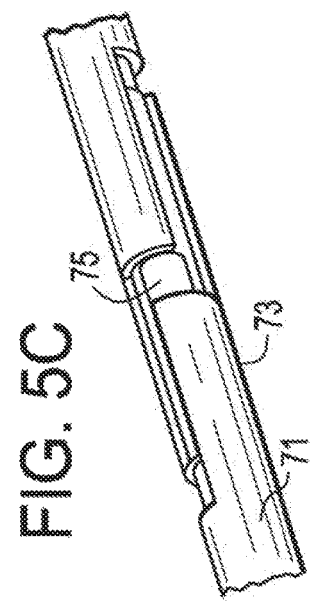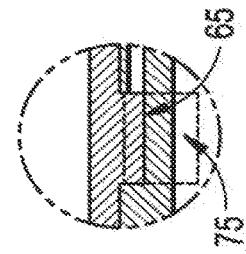

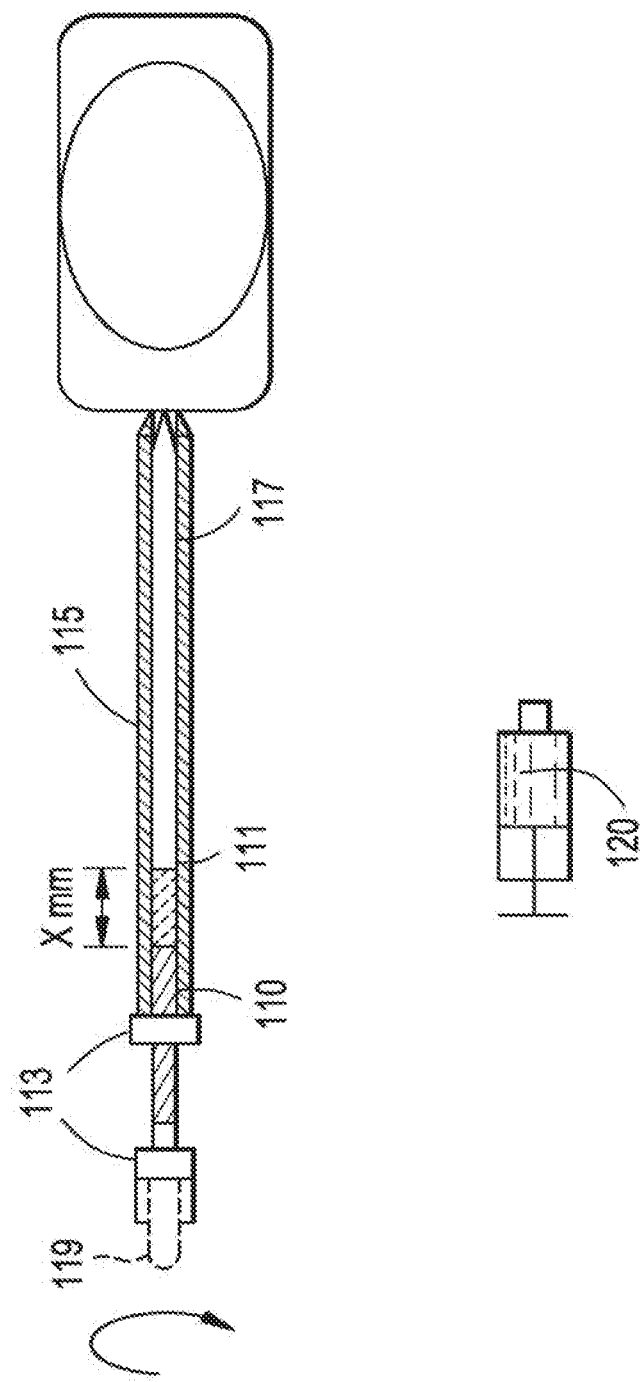

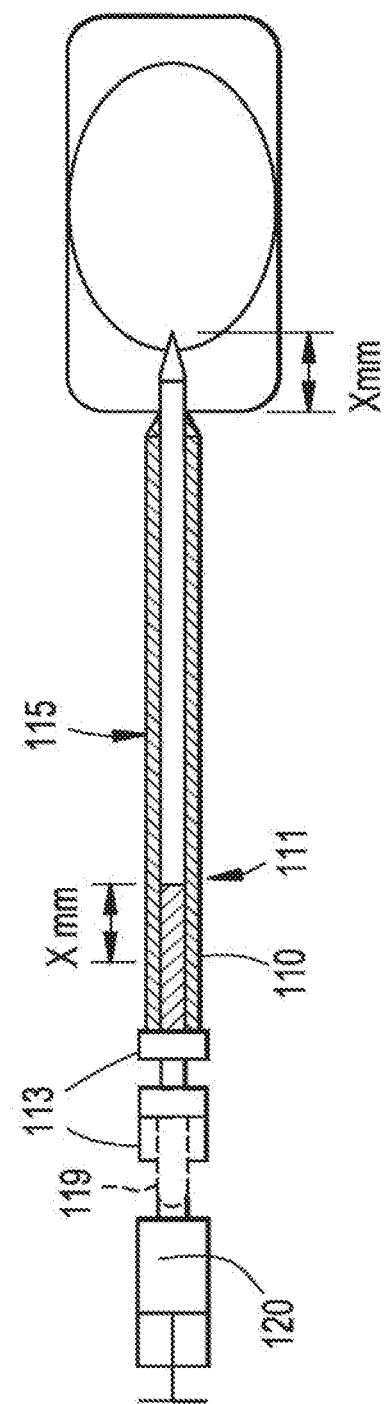

INTERVERTEBRAL DISC PUNCTURE AND TREATMENT SYSTEM

INCORPORATION BY REFERENCE STATEMENT

The present application claims priority to and is a continuation of the patent application identified by U.S. Ser. No. 15/061,786, filed Mar. 4, 2016, now patented as U.S. Pat. No. 10,349,928, which is a continuation of patent application identified by U.S. Ser. No. 11/422,222, filed Jun. 5, 2006, now abandoned, all of which the entire contents of which are hereby incorporated herein by reference.

BACKGROUND

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases ("MMPs"). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells to emit larger than normal amounts of the above-mentioned cytokines. In other instances of DDD, genetic factors, such as programmed cell death, or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins.

As DDD progresses, the toxic levels of the cytokines present in the nucleus pulposus begin to degrade the extracellular matrix. In particular, the MMPs (under mediation by the cytokines) begin cleaving the water-retaining portions of the proteoglycans, thereby reducing their water-retaining capabilities. This degradation leads to a less flexible nucleus pulposus, and so changes the load pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

US Published Patent Application 2004/0229878 discloses a procedure for the intradiscal administration of therapeutics, wherein an outer needle and an inner stylet are advanced to the annulus fibrosus, the stylet is withdrawn and replaced with an inner needle attached to a syringe, and the inner needle is advanced to the nucleus pulposus for injection of the therapeutic into the nucleus pulposus.

In other approaches, a single, fine gauge needle is used to penetrate the skin and musculature approaching the intervertebral disc. However, the drawbacks of this approach include the need for a relatively sturdy needle and an increase in the risk of infection to the disc (due to the fact that the needle that pierces the skin is also the needle that enters the disc).

To reduce the risk of infection and subsequent discitis that may result from percutaneous procedures, one common practice is to use a double needle approach in which a larger gauge needle is used to penetrate the skin and a second finer, gauge needle is passed through the first needle and into the intervertebral disc. However, this approach requires two separate needles and manual insertion of the second needle inside of the first.

Some needle systems developed for use outside of the disc area have dual needle designs. For example, in needle systems unrelated to intradiscal delivery of therapeutics, various needle systems and procedures are employed for aspirating body fluids, and some of these employ concentric multi-gauge needles. Various access needle systems designed to treat ailing tissue are made to allow a second device to pass through an outer access needle. Various extendable/retractable needle systems exist as safety devices to prevent user injury by needle sticks.

U.S. Pat. Nos. 5,871,470 and 6,245,044 disclose a set of interlocking concentric epidural-spinal needles for delivery of medicaments into the epidural and subarachnoid spaces. However, these systems contain two separate needles that the user must assemble. Neither system is pre-assembled.

U.S. Pat. Nos. 6,497,686 and 6,695,822 disclose a method and device for performing sterile endoluminal procedures using a needle system that includes two concentric needles. However, these systems do not allow for aspiration of the medicament into an attached syringe. Moreover, the distal portion of the device is designed to remain in place after the procedure is completed.

BRIEF SUMMARY OF THE DRAWINGS

It is an object of the present invention to provide simple and safe percutaneous access to the intervertebral disc for intradiscal delivery of therapeutic agents to the disc.

The present inventors have developed a pre-assembled, telescoping needle system comprising an outer needle surrounding a finer gauge inner needle. After percutaneous penetration by the outer needle and its advance to the annulus fibrosus, the inner needle is moved distally to extend past the outer needle and penetrate the intervertebral disc. A therapeutic agent may then be delivered from a syringe through the inner needle and into the nucleus pulposus.

The needle system of the present invention provides a number of advantages over the conventional intradiscal needle systems.

First, the needle system is pre-assembled. This enables both ease of use by the clinician and a reduced diameter of the inner (injection) needle, as it is supported by the outer needle during its insertion at the disc site.

Second, there is a reduced risk of discitis (intradiscal infection). The inner injection needle is shielded by the outer cannula from contact or exposure to the operative environment, skin and soft inner tissues. This reduced exposure yields a reduced infection potential.

Third, the invention provides a controlled discal injection depth. The present invention allows for placement of the tip of the outer needle at or upon the outer rim of the annulus fibrosus, and subsequent advancement of the inner needle into the disc space. Controlled and monitored advancement of the inner needle into the disc space allows for predetermination or measured determination of intradiscal injection depths and associated location.

Therefore, in accordance with the present invention, there is provided a method of delivering a therapeutic agent to an intervertebral disc having an annulus fibrous and a nucleus pulposus, comprising the steps of:
a) providing a therapeutic delivery system, comprising:
   i) an outer needle having a distal end, and
   ii) an inner needle received within the outer needle and having a distal end,
b) inserting the outer needle into the patient at a location dorsal of the intervertebral disc,
c) advancing the outer needle to abut the annulus fibrosus, and then
d) advancing only the inner needle into the nucleus pulposus.

DESCRIPTION OF THE FIGURES

FIG. 1A discloses a cross section of the needle system of the present invention having a ball detent locking mechanism, prior to its deployment into an intervertebral disc.

FIG. 1B is an enlarged cross section of the locking mechanism of FIG. 1A.

Figure 2:
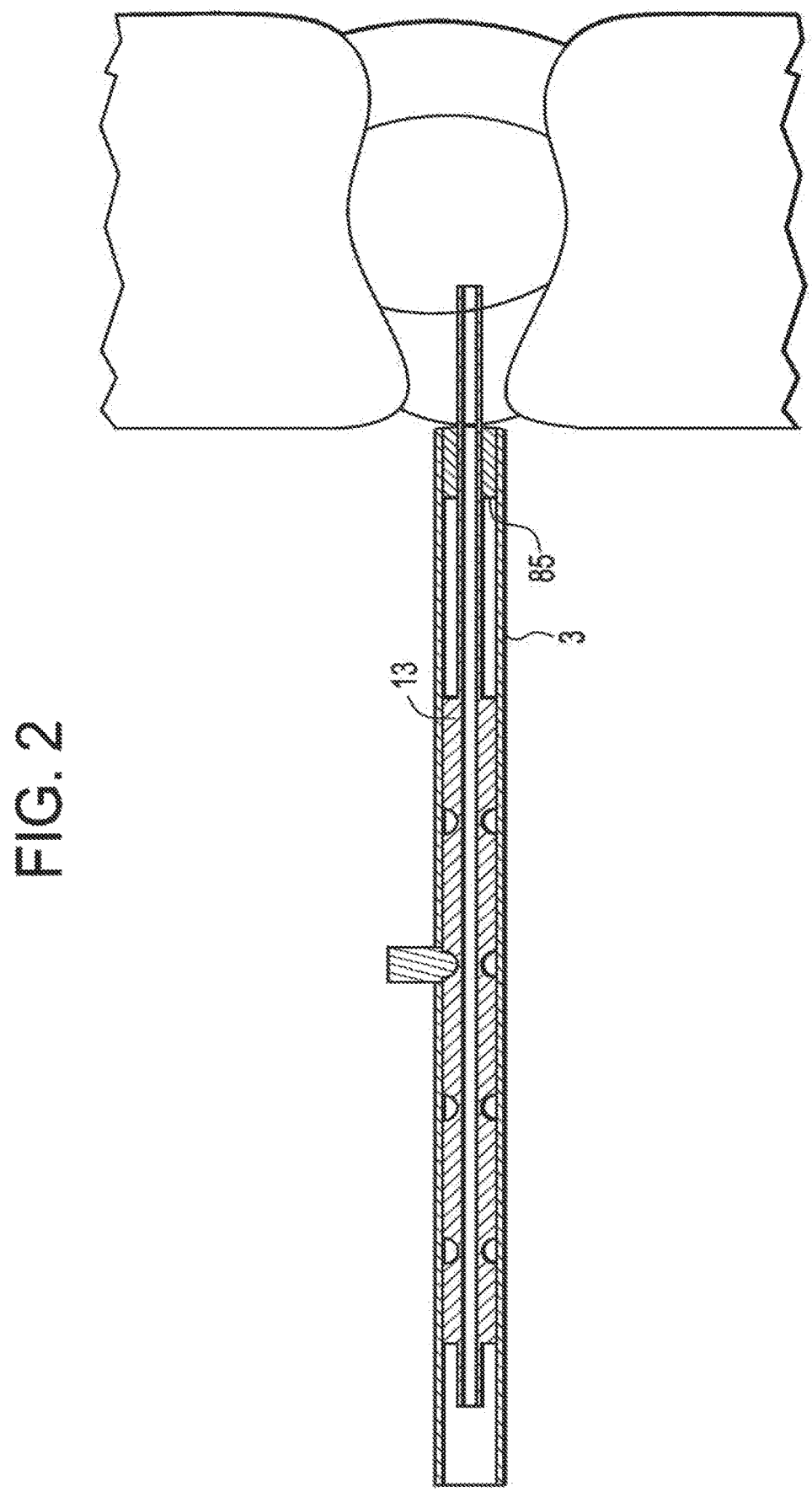

FIG. 2 discloses a cross section of the needle system of FIG. 1A, after its deployment into an intervertebral disc.

FIG. 3A discloses a cross section of the needle system of the present invention having a threaded locking mechanism, prior to its deployment into an intervertebral disc.

FIG. 3B is an enlarged cross section of the locking mechanism of FIG. 3A.

FIG. 4 discloses a cross section of the needle system of FIG. 3A, after its deployment into an intervertebral disc.

FIG. 5A discloses a cross section of the needle system of the present invention having a keyed locking mechanism, prior to its deployment into an intervertebral disc.

FIG. 5B is an enlarged cross section of the locking mechanism of FIG. 5A.

FIG. 5C is a perspective view of the inner needle of FIG. 5A having a channel herein.

Figure 6:
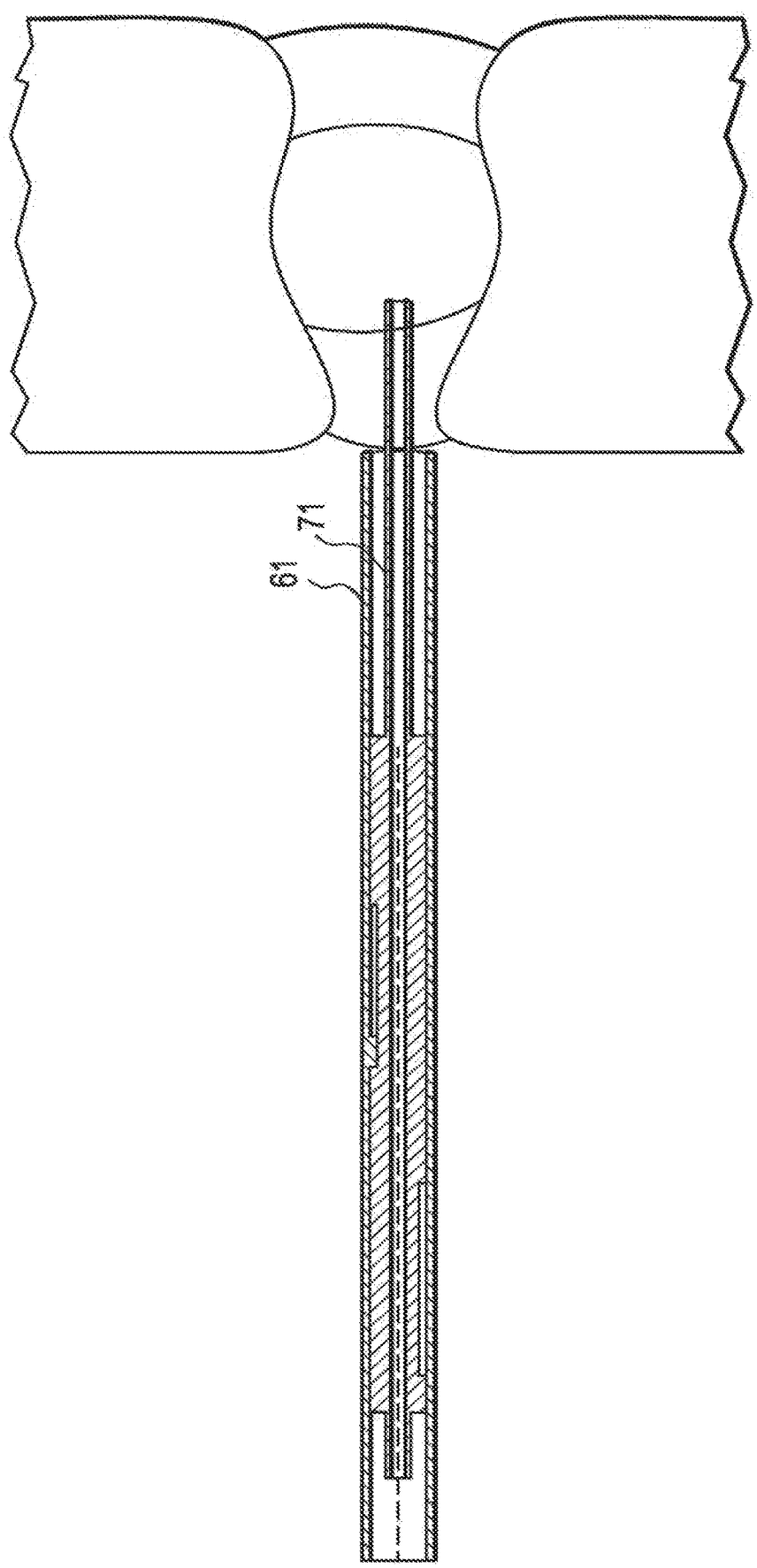

FIG. 6 discloses a cross section of the needle system of FIG. 5A, after its deployment into an intervertebral disc.

Figure 7A:
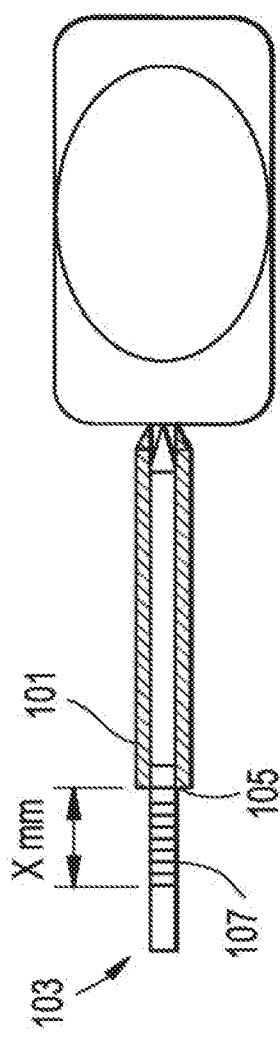
Figure 7B:
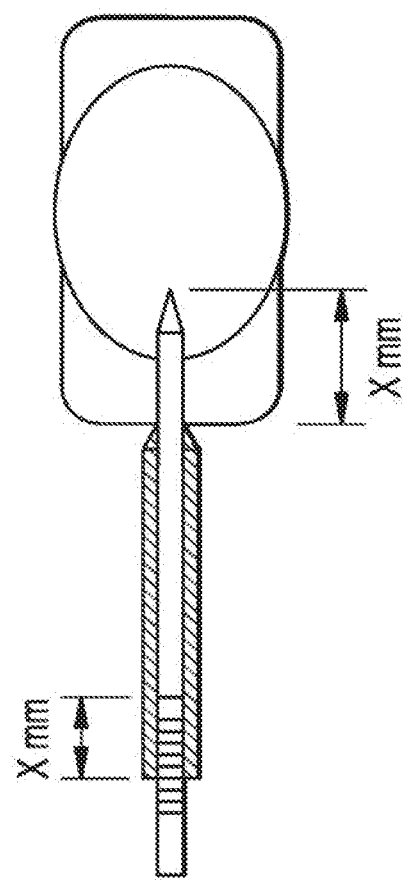

FIGS. 7a-7b disclose cross sections of generalized needle systems of the present invention.

FIGS. 8a-8b disclose cross sections of needle systems of the present invention having threaded advancement.

FIGS. 9a-9d disclose cross sections of needle systems of the present invention having keyed advancement.

DETAILED DESCRIPTION OF THE INVENTION

The present invention comprises a dual needle intradiscal device comprising a larger gauge outer needle and a smaller gauge inner needle. Preferably, the needles are sized for intradiscal injection through a percutaneous approach.

The outer needle serves as the access needle, as it functions to pierce and penetration the patient's skin and muscle up to the annulus fibrosus. Further, it functions as a shield for the inner needle prior to its entry into the disc, thereby minimizing the chances of the inner needle infecting the disc and subsequent discitis. Preferably, the outer needle has a sufficient stiffness and length to penetrate the skin and underlying muscle, and is more preferably between 10 gauge and 20 gauge in bore diameter and between 8 cm and 20 cm in length.

The inner needle has a length sufficient to penetrate the annulus fibrosus region of the disc, and is typically between 4 cm and 10 cm longer than the outer needle. In order to minimize damage to the intervertebral disc, the inner needle should be a fine gauge needle, preferably between 22 gauge and 32 gauge. The proximal end of the inner needle can attach to a standard syringe.

Preferably, the position of the outer needle can be advanced and then fixed at various positions along the axis of the inner needle according to the needs of the clinician. This is preferably accomplished with a locking mechanism.

For example, in one embodiment, the inner needle is first set in a first locked position to extend about 0.5 cm to 1 cm beyond the outer needle so that medicament can be aspirated proximally into the syringe through the distal end of the inner needle. Once the medicament has been aspirated into the syringe, the locking mechanism can be unlocked and the inner needle retracted and fixed at a new position such it sits 0.5 cm to 1 cm proximal to the distal end of the outer needle. In this second locked position, the needle system can be inserted through the patient's skin. When the outer needle has penetrated to a sufficient depth (such as up to the annulus fibrosus), the locking mechanism can again be unlocked and the inner needle can slide distally relative to the outer needle and penetrate the disc.

In some preferred embodiments, the locking mechanism is provided via a ball detent mechanism. Now referring to FIGS. 1A and 1B, in some embodiments, there is provided a needle system 1 for intradiscal delivery of a therapeutic agent, comprising:
a) an outer needle 3 having an outer surface 5 having a transverse throughhole 7, and a detent 9 provided in the throughhole, the detent having a projection 11 extending inwardly, and
b) an inner needle 13 having an outer surface 15 having a plurality of axially spaced grooves 17, wherein the projection of the detent is shaped to be received in the plurality of axially spaced grooves.

In some embodiments thereof, the outer surface of the outer needle has a hole therein into which a pushbutton detent is releasably provided. The outer surface of the inner needle contains a plurality of grooves spaced at predetermined intervals. When the push button of the outer needle is engaged with groove of the inner needle, the needle system is locked and the relative axial positions of the two needles are fixed. When the push button of the outer needle is disengaged from a groove of the inner needle, the system is unlocked and the inner needle may be moved forward or backward relative to the outer needle (or vice versa). FIG. 2 shows the distal movement of the inner needle 13 by a single stop interval as compared to its position in FIG. 1A.

In some preferred embodiments, the locking mechanism is provided via a pair of mating threads. In these embodiments, the inner needle can be threadably connected to the outer needle and advanced to a desired depth in the disc by rotation of the inner needle within the outer needle. Now referring to FIGS. 3A and 3B, in some embodiments, there is provided a needle system 21 for intradiscal delivery of a therapeutic agent, comprising:
a) an outer needle 23 having an inner surface 25 having a first thread 27, and
b) an inner needle 31 having an outer surface 33 having a second thread 35, wherein the first thread is adapted to mate with the second thread.

When one of the needles is rotated in respect to the other needle, the relative rotation of the engaged threads is such that axial movement of the inner needle is accomplished.

FIG. 4 shows the distal movement of the inner needle produced by relative rotation of the threads, as compared to its position in FIG. 3A.

Now referring to FIG. 5A-5C, in some embodiments, the stops are provided by a keyed mechanism. In FIGS. 5A-5C, there is provided a needle system 51 for intradiscal delivery of a therapeutic agent, comprising:
a) an outer needle 61 having an inner surface 63 having a tab 65 extending therefrom, and
b) an inner needle 71 having an outer surface 73 having a channel 75 therein, wherein the tab is received in the channel.

In preferred embodiments thereof, the inner diameter of the outer needle has a tab extending therefrom, while the outer diameter of the inner needle has a channel therein, wherein the channel has alternating axial and lateral portions defining a plurality of stop intervals. In use, the clinician moves the inner needle distally until the tab of the outer needle abuts the lateral portion of the inner needle. If the clinician desires to move the inner needle distally again, the clinician rotates the inner needle so that the tab moves along the lateral portion of the channel and enters the next axial portion of the channel. The clinician then moves the inner needle axially once again, with the channel of the inner needle being guided by the tab, until the tab of the outer needle abuts the next lateral portion of the inner needle.

FIG. 6 shows the distal movement of the inner needle produced by movement of the tab in the channel, as compared to its position in FIG. 5A.

In other embodiments using a keyed locking mechanism, the inner surface of the outer needle has the channel and the outer surface of the inner needle has the tab. In one preferred embodiment, the keyed locking mechanism includes a simple twist-lock mechanism such that in two predetermined rotational positions (e.g., 0° and either 45°, 90°, 180°, or 270°), the outer needle can slide relative to the inner needle.

In some embodiments using a locking mechanism, and now referring to FIG. 1A, the inner needle has a first proximal outer diameter 81 and a second distal outer diameter 83, wherein the first proximal outer diameter is greater than the second distal outer diameter. This embodiment minimizes the diameter of the portion of the needle that penetrates the annulus fibrosus, thereby reducing injury to the annulus fibrosus. In some embodiments thereof, the system further comprises an annular plug 85 disposed within the distal end of the outer needle and adapted to fit between the inner and outer needles. The annular plug prevents fluid from entering the bore of the outer needle when the inner needle has a reduced diameter and provides a guide for the distal advance of the inner needle. In this embodiment, the first proximal outer diameter is preferably sized to be slightly less than the inner diameter of the outer needle, so that the locking mechanism (whether it be a ball detent mechanism, a pair of threads, or a keyed mechanism) possesses a snug fit.

In some embodiments, after the medicament is administered, the locking mechanism can be re-engaged and the two needles can be removed together from the patient. In other embodiments, after the medicament is administered, the locking mechanism remains disengaged and the two needles are removed independently.

In some embodiments wherein only the inner needle is removed, a second needle can be inserted through the same outer needle. In some embodiments thereof, this second inner needle may be a standard needle that does not lock to the outer needle. In other embodiments thereof, this second inner needle may comprise a locking feature that is engageable with a locking feature of the outer needle.

In some embodiments, depth markings can be provided to allow the clinician to measure the depth of discal entry and location of the treatment within the nucleus pulposus, and thereby control the depth of discal entry and location of the treatment within the nucleus pulposus.

The needle system of the present invention can be suitably used to inject therapeutic agents into intravertebral disc and synovial joints (such as facet joints, hip joints and knee joints). It may be used in the aspiration of bone marrow or for biopsy procedures.

In some embodiments, the therapeutic materials disclosed in US Published Patent Application 2004/0229878, which is incorporated by reference in its entirety, are injected into the disc.

FIGS. 7a and 7b depict the general concept of the Intervertebral Puncture and Treatment System in its respective pre-insertion and post-insertion modes. During pre-insertion, and now referring to FIG. 7a, the tips of the outer cannula 101 and inner needle 103 are aligned and advanced until disc contact is observed. In some embodiments thereof, the outer cannula is about 18 gauge RW, with a 0.033 inch ID and a 0.050 inch OD, while the inner delivery needle is about 22 gauge RW, with a 0.016 inch ID and a 0.028 inch OD. Also shown is a generalized representation of a depth control means 105 (that is enabled in subsequent figures by threaded advancement and keyway stops). Depth control markings 107 correspond to the insertion depth (x mm) into the disc following contact with the annular wall, as can be seen in the post-insertion image FIG. 7b.

Now referring to FIG. 8a, there is provided a more detailed embodiment depicted device orientation pre-insertion into the disc. This device has a threaded advancement means 110 and a positive depth stop 111 (as shown by ghost threads) at an insertion depth of x mm. Handles 113 are provided on each of the outer cannula 115 and inner needle 117 to assist in threading the inner needle into the outer cannula. Also shown in this FIG. 8a is the treatment attachment location 119 (which may be, for example, a luer slip, luer lock, or injection cap) at which the device is attached to a treatment container 120 (which may be, for example, a syringe, vial, bag, or pouch).

FIG. 8b discloses the threaded advancement device of FIG. 8a following insertion into the disc. In this case, threaded advancement of the inner needle has been stopped by the positive depth stop 111 (provided by the end of the threads) at a predetermined depth of x mm. Also shown in this figure are handles 113, outer cannula 115, inner needle 117, and the treatment container 120 attached to the inner needle 117 at treatment attachment location 119 for dispensing at desired depth.

Figure 9A:
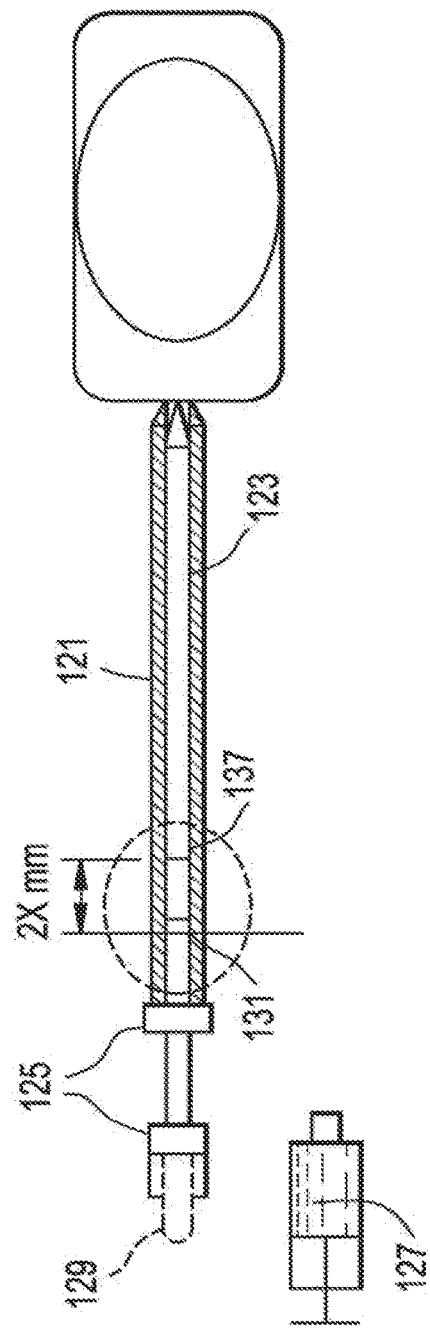
Figure 9B:
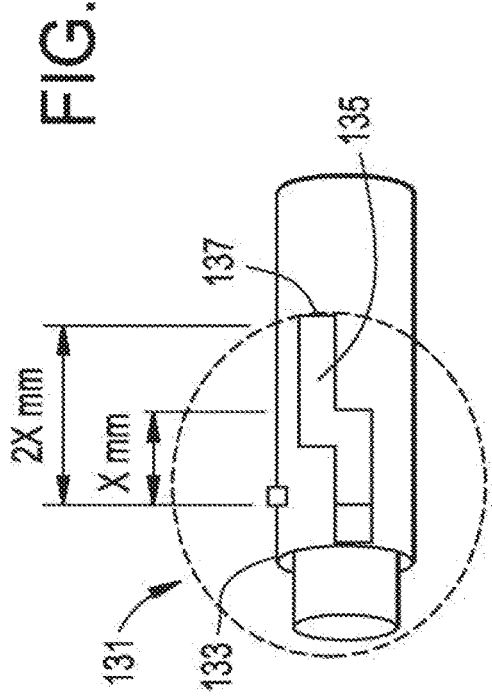

Now referring to FIGS. 9a and 9b, there is provided a device having an outer cannula 121, an inner needle 123, advancement handles 125, a treatment container 127 attached to the inner needle at a treatment location 129, and keyed advancement means 131 in its pre-insertion configuration. The key 133 is located on either the outer and inner needle (shown here on the inner needle as a protrusion) and is disposed within keyway 135. The distance between the key and the keyway stop 137 will control the depth of intradiscal insertion (2x mm) following contact with the annulus.

Figure 9C:
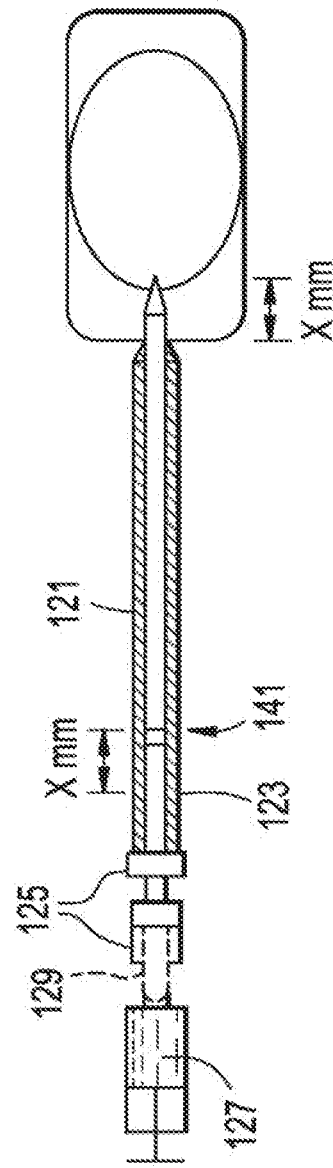
Figure 9D:
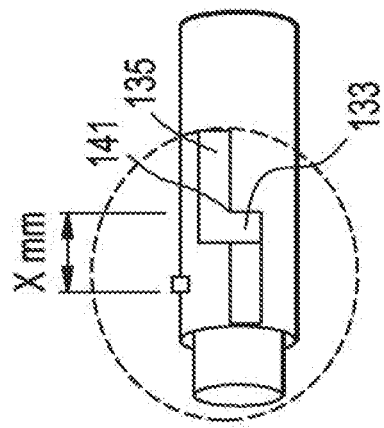

Now referring to FIGS. 9c and 9d, there is provided the device of FIGS. 9a and 9b in its post-insertion configuration.

In this case, inner needle 123 and its accompanying key 133 have been advanced until the keyway stop is contacted (x mm). Additional advancement of the inner needle (for example, 2x mm) may be obtained by rotating the inner needle (for example, 90 degrees) and applying an advancement force until the second key way stop is contacted.

EXAMPLE

This non-limiting prophetic example describes how to transdiscally administer a formulation comprising a therapeutic agent and saline into a nucleus pulposus of a degenerating disc.

First, a clinician uses a diagnostic test to verify that a particular disc within a patient has high levels of a particular pro-inflammatory cytokine.

Next, the clinician provides a local anesthetic (such as 5 ml lidocaine) to the region dorsal of the disc of concern to reduce subcutaneous pain.

Next, the clinician punctures the skin of the patient dorsal the disc of concern with a relatively large (e.g., 18-19 gauge) needle having a smaller gauge needle contained therein, and advances the needle through subcutaneous fat and dorsal sacrolumbar ligament and muscles to the outer edge of the intervertebral disc. The proximal end opening of the smaller needle is fluidly connected to a syringe. The barrel of the syringe contains the formulation of the present invention. The formulation contains REMICADE® infliximab, and has an infliximab concentration of between about 30 mg/ml and about 60 mg/ml.

Next, the physician advances the smaller needle co-axially through the larger needle and past the distal end of the larger needle, thereby puncturing the annulus fibrosus. The smaller needle is then further advanced into the center of the nucleus pulposus. Finally, the clinician depresses the plunger of the syringe, thereby injecting between about 0.1 and 1 ml of the formulation into the nucleus pulposus.

What is claimed is:

1. A method of treating a patient having degenerative disc disease (DDD), comprising:
   inserting into a selected tissue of a patient at least a portion of a distal end of an elongate device comprising:
   i) an outer tube having a substantially smooth outer surface, a distal end, and a proximal end, and
   ii) an inner elongate member housed within the outer tube, the inner elongate member having a distal end and a proximal end;
   advancing at least a portion of the elongate device within the selected tissue of the patient, wherein the distal end of the outer tube of the elongate device is positioned at a location near an outer wall of an annulus fibrosus of an intervertebral disc;
   projecting the inner elongate member out of the distal end of the outer tube whereby at least a portion of the distal end of the inner elongate member penetrates into the annulus fibrosus of the intervertebral disc while the outer tube remains outside the annulus fibrosus; and
   exposing the selected tissue to a sensing element associated with the distal end of the elongate device.

2. The method of claim 1, wherein the outer tube of the elongate device has a transverse through hole.

3. The method of claim 1, wherein the inner elongate member projects into the nucleus pulposus.

4. The method of claim 1, wherein the sensing element is located at the distal end of the inner elongate member of the elongate device.

5. The method of claim 1, wherein the sensing element is emitted at the distal end of the inner elongate member into the selected tissue.

6. The method of claim 1, wherein the projecting step comprises rotating a threaded component.

7. The method of claim 1, wherein the elongate device is pre-assembled prior to insertion into the selected tissue of the patient.

8. A method of treating a patient having degenerative disc disease (DDD), comprising:
   minimally invasively inserting into a selected tissue of a patient at least a portion of a distal end of an elongate device comprising:
   i) an outer tube having a substantially smooth outer surface, a distal end, and a proximal end; and
   ii) an inner elongate member housed within the outer tube, the inner elongate member having a distal end and a proximal end;
   assessing the selected tissue of the patient by applying a current to the selected tissue; and
   obtaining a quantified value in the selected tissue from the assessment, wherein, if the quantified value is greater than a second value, projecting the inner elongate member out of the distal end of the outer tube whereby at least a portion of the distal end of the inner elongate member penetrates into the annulus fibrosus of the intervertebral disc while the outer tube remains outside the annulus fibrosus.

9. The method of claim 8, further comprising exposing the selected tissue to a sensing element associated with the distal end of the elongate device.

10. The method of claim 9, wherein the sensing element is located at the distal end of the inner elongate member of the elongate device.

11. The method of claim 8, further comprising projecting the inner elongate member out of the distal end of the outer tube whereby the distal end of the inner elongate member penetrates into the annulus fibrosus of the intervertebral disc.

12. The method of claim 8, wherein the projecting step comprises rotating a threaded component.

13. The method of claim 8, wherein the inner elongate member projects into the nucleus pulposus.

14. The method of claim 8, wherein the elongate device is pre-assembled prior to insertion into the selected tissue of the patient.

15. A method of treating a patient having degenerative disc disease (DDD), comprising:
   minimally invasively inserting into a selected tissue of a patient at least a portion of a distal end of an elongate device comprising:
   i) an outer tube having a substantially smooth outer surface, a distal end, and a proximal end; and
   ii) an inner elongate member housed within the outer tube, the inner elongate member having a distal end and a proximal end, and wherein the distal end of the outer tube is positioned at a location outside of an annulus fibrosus of an intervertebral disc;
   assessing the selected tissue of the patient by applying a current to the selected tissue; and
   obtaining a quantified value in the selected tissue from the assessment, wherein, if the quantified value is greater than a second value, simultaneously rotating and advancing at least a portion of the inner elongate member within the selected tissue of the patient, whereby at least a portion of the distal end of the inner elongate member penetrates into the annulus fibrosus while the outer tube remains outside the annulus fibrosus.

16. The method of claim 15, further comprising exposing the selected tissue to a sensing element associated with the distal end of the elongate device.

17. The method of claim 16, wherein the sensing element is located at the distal end of the inner elongate member of the elongate device.

18. The method of claim 15, further comprising projecting the inner elongate member out of the distal end of the outer tube whereby the distal end of the inner elongate member penetrates into the annulus fibrosus of the intervertebral disc.

19. The method of claim 15, wherein the inner elongate member projects into the nucleus pulposus.

20. The method of claim 15, wherein the elongate device is pre-assembled prior to insertion into the selected tissue of the patient.

* * * * *